(12) United States Patent
Pickup et al.

(10) Patent No.: US 10,197,539 B2
(45) Date of Patent: Feb. 5, 2019

(54) SYSTEM AND METHOD FOR ASSESSING A CALIBRATION OF A MULTI-AXIS ULTRASONIC SCANNER

(71) Applicant: BAE Systems plc, London (GB)

(72) Inventors: Kevin John Pickup, Balderstone (GB); Olivia Clare Mason, Balderstone (GB)

(73) Assignee: BAE Systems Plc, London (GB)

(*) Notice: Subject to any disclaimer, the term of this patent is extended or adjusted under 35 U.S.C. 154(b) by 0 days.

(21) Appl. No.: 15/540,184

(22) PCT Filed: Jan. 5, 2016

(86) PCT No.: PCT/GB2016/050006
§ 371 (c)(1),
(2) Date: Jun. 27, 2017

(87) PCT Pub. No.: WO2016/110682
PCT Pub. Date: Jul. 14, 2016

(65) Prior Publication Data
US 2018/0267000 A1 Sep. 20, 2018

(30) Foreign Application Priority Data

Jan. 5, 2015 (EP) .................................. 15275001
Jan. 5, 2015 (GB) ................................... 1500052.4

(51) Int. Cl.
*G01N 29/30* (2006.01)
(52) U.S. Cl.
CPC .................................. *G01N 29/30* (2013.01)
(58) Field of Classification Search
CPC ....... G01N 29/30; B25J 9/1692; G01B 21/02; G01H 3/005
(Continued)

(56) References Cited

U.S. PATENT DOCUMENTS 5,837,880 A 11/1998 Shakinovsky et al.
6,078,846 A * 6/2000 Greer ..................... B25J 9/1692
700/174
(Continued)

FOREIGN PATENT DOCUMENTS

DE 3018092 A1 11/1981
DE 29618726 U1 2/1997
(Continued)

OTHER PUBLICATIONS

International Preliminary Report on Patentability for International Application No. PCT/GB2016/050006, dated Jul. 11, 2017, 7 pages.
(Continued)

*Primary Examiner* — Robert R Raevis
(74) *Attorney, Agent, or Firm* — Maine Cernota & Rardin (57) ABSTRACT

A method and apparatus for assessing a calibration of a multi-axis ultrasonic scanner, the method comprising: providing a calibration verification tool (100), comprising a plurality of mutually oblique plates (110-140) defining surfaces at predefined angles with respect to one another; providing a digital model of the tool; registering, by the ultrasonic scanner, the tool (100) within the reference frame; controlling the ultrasonic scanner to measure a plate (110-140) to determine a reference signal; measuring each plate (110-140); using the reference signal and the plate measurements, determining an orientation of the ultrasonic scanner when each plate was measured; and, using the determined orientations, verifying whether or not the ultrasonic scanner calibration.

14 Claims, 3 Drawing Sheets

(58) Field of Classification Search
USPC ....... 73/1.75, 1.79, 1.81, 1.82, 1.86; 702/94, 702/95, 103
See application file for complete search history.

(56) References Cited

U.S. PATENT DOCUMENTS

| | | |
|---|---|---|
| 2005/0068523 A1 | 3/2005 | Wang et al. |
| 2007/0271995 A1 | 11/2007 | Orchard |
| 2015/0088311 A1* | 3/2015 | Suzuki .................. B25J 9/1697 700/254 |

FOREIGN PATENT DOCUMENTS

| | | |
|---|---|---|
| EP | 1091186 A2 | 4/2001 |
| EP | 1698954 A1 | 9/2006 |
| EP | 3009836 A1 | 4/2016 |
| KR | 1020110032562 A | 3/2011 |
| WO | 9013024 A1 | 11/1990 |
| WO | 216865 A2 | 2/2002 |

OTHER PUBLICATIONS

International Search Report and Written Opinion of International Application No. PCT/GB2016/050006, dated Apr. 12, 2016, 11 pages.
Extended European Search Report of European Application No. EP15275001.4, dated Jul. 1, 2015, 6 pages.
Search Report under Section 17(5) of Great Britain Application No. GB1500052.4, dated Jun. 18, 2015, 4 pages.
Combined Search and Examination Report under Section 17 and 18(3) of Great Britain Application No. GB16001232, dated Jun. 23, 2016, 5 pages.

* cited by examiner

SYSTEM AND METHOD FOR ASSESSING A CALIBRATION OF A MULTI-AXIS ULTRASONIC SCANNER

RELATED APPLICATIONS

This application is a National Phase application filed under 35 USC § 371 of PCT Application No. PCT/GB2016/050006 with an International filing date of Jan. 5, 2016 which claims priority of GB Patent Application 1500052.4 filed Jan. 5, 2015 and EP Patent Application 15275001.4 filed Jan. 5, 2015. Each of these applications is herein incorporated by reference in its entirety for all purposes.

FIELD OF THE INVENTION

The present invention relates to systems and methods for assessing a calibration of a multi-axis ultrasonic scanner.

BACKGROUND

It is desirable to verify the calibration and control of rotational axes for an automated multi-axis ultrasonic scanning machine.

It is desirable to determine whether or not the actual movement of a scan head (i.e. a manipulator head) of the multi-axis ultrasonic scanning machine is the same as the movement instructed by a controller of the scan head.

It is desirable to validate movement of the scan head along both a single axis and along multiple axes.

However, using mathematical design parameters of gearing ratios and/or kinematic models of the ultrasonic scanning machine to perform this verification tends to be difficult.

SUMMARY OF THE INVENTION

The present inventors have realised that a physical test piece could be used to perform calibration verification of ultrasonic scanning machines, and, moreover, that such a physical test piece is useable by different types of ultrasonic scanners, including both immersion and squirter rigs.

In a first aspect, the present invention provides a method of assessing a calibration of a multi-axis ultrasonic scanner. The method comprises: providing a calibration verification tool, the tool comprising a plurality of mutually oblique plates defining a plurality of mutually oblique planar surfaces, the surfaces being at predefined angles with respect to one another; providing a digital model of the tool defined in a coordinate reference frame of the multi-axis ultrasonic scanner; registering, by the multi-axis ultrasonic scanner, the tool within the coordinate reference frame of the multi-axis ultrasonic scanner; using the digital model, controlling the multi-axis ultrasonic scanner to measure a physical property of a plate of the tool, thereby determining a reference signal; for each plate in the plurality of mutually oblique plates, using the digital model, controlling the multi-axis ultrasonic scanner to measure the physical property of that plate; for each plate in the plurality of mutually oblique plates, using the reference signal and the measured physical property of that plate, determining an orientation within the coordinate reference frame of at least part of the multi-axis ultrasonic scanner when the physical property of that plate was measured; and, using the determined orientations, verifying whether or not the multi-axis ultrasonic scanner is calibrated such that one or more predetermined criteria are satisfied.

Measuring the physical property of a plate to determine the reference signal may include optimising a received response from that plate, i.e. the reference signal may be an optimised response from a plate.

The physical property may be a direct reflected ultrasonic response.

Each plate may comprise opposing upper and lower surfaces. Measuring the physical property of a plate may include measuring the physical property from both upper and lower surfaces of that plate. Measuring the physical property of a plate may include measuring a transmitted ultrasonic signal through that plate.

The step of determining orientations may comprise, for each plate in the plurality of mutually oblique plates, comparing the measured physical property of that plate to the reference signal, and based on the comparison, determining the orientation within the reference frame of the at least part of the multi-axis ultrasonic scanner when the physical property of that plate was measured.

The calibration verification tool may further comprise a plurality of reference features. The digital model may comprise a plurality of digital reference features, the digital reference features having the same positions on the digital model and the reference features have on the tool. The step of registering may comprise: measuring, by the multi-axis ultrasonic scanner, the positions of the reference features; and registering the measured reference features with the digital reference features, thereby determining a position of the tool in the coordinate reference frame of the multi-axis ultrasonic scanner.

In a further aspect, the present invention provides a system comprising: a calibration verification tool, the tool comprising a plurality of mutually oblique plates defining a plurality of mutually oblique planar surfaces, the surfaces being at predefined angles with respect to one another; one or more processors comprising a digital model of the tool defined in a coordinate reference frame of the multi-axis ultrasonic scanner; and a controller operatively coupled to the one or more processors. The controller is configured to: control the multi-axis ultrasonic scanner to register the tool within the coordinate reference frame of the multi-axis ultrasonic scanner; using the digital model, control the multi-axis ultrasonic scanner to measure a physical property of a plate of the tool, thereby determining a reference signal; and, for each plate in the plurality of mutually oblique plates, using the digital model, control the multi-axis ultrasonic scanner to measure the physical property of that plate. The one or more processors are configured to: for each plate in the plurality of mutually oblique plates, using the reference signal and the measured physical property of that plate, determine an orientation within the coordinate reference frame of at least part of the multi-axis ultrasonic scanner when the physical property of that plate was measured; and, using the determined orientations, verify whether or not the multi-axis ultrasonic scanner is calibrated such that one or more predetermined criteria are satisfied.

The calibration verification tool may comprise at least sixteen mutually oblique plates. An angle between a first surface of the plurality of surfaces and a direction along an x-axis of a Cartesian coordinate system may be 0°. An angle between the first surface and a direction along a y-axis of the Cartesian coordinate system may be 0°. An angle between a second surface of the plurality of surfaces and the direction along the x-axis may be $\theta_1$. An angle between the second surface and the direction along the y-axis may be 0°. An angle between a third surface of the plurality of surfaces and the direction along the x-axis may be $\theta_2$. An angle between the third surface and the direction along the y-axis may be 0°. An angle between a fourth surface of the plurality of surfaces and the direction along the x-axis may be $\theta_3$. An angle between the fourth surface and the direction along the y-axis may be 0°. An angle between a fifth surface of the plurality of surfaces and the direction along the x-axis may be 0°. An angle between the fifth surface and the direction along the y-axis may be $\varphi_1$. An angle between a sixth surface of the plurality of surfaces and the direction along the x-axis may be 0°. An angle between the sixth surface and the direction along the y-axis may be $\varphi_2$. An angle between a seventh surface of the plurality of surfaces and the direction along the x-axis may be 0°. An angle between the seventh surface and the direction along the y-axis may be $\varphi_3$. An angle between a eighth surface of the plurality of surfaces and the direction along the x-axis may be $\theta_1$. An angle between the eighth surface and the direction along the y-axis may be $\varphi_1$. An angle between a ninth surface of the plurality of surfaces and the direction along the x-axis may be $\theta_2$. An angle between the ninth surface and the direction along the y-axis may be $\varphi_1$. An angle between a tenth surface of the plurality of surfaces and the direction along the x-axis may be $\theta_3$. An angle between the tenth surface and the direction along the y-axis may be $\varphi_1$. An angle between a eleventh surface of the plurality of surfaces and the direction along the x-axis may be $\theta_1$. An angle between the eleventh surface and the direction along the y-axis may be $\varphi_2$. An angle between a twelfth surface of the plurality of surfaces and the direction along the x-axis may be $\theta_2$. An angle between the twelfth surface and the direction along the y-axis may be $\varphi_2$. An angle between a thirteenth surface of the plurality of surfaces and the direction along the x-axis may be $\theta_3$. An angle between the thirteenth surface and the direction along the y-axis may be $\varphi_2$. An angle between a fourteenth surface of the plurality of surfaces and the direction along the x-axis may be $\theta_1$. An angle between the fourteenth surface and the direction along the y-axis may be $\varphi_3$. An angle between a fifteenth surface of the plurality of surfaces and the direction along the x-axis may be $\theta_2$. An angle between the fifteenth surface and the direction along the y-axis may be $\varphi_3$. An angle between a sixteenth surface of the plurality of surfaces and the direction along the x-axis may be $\theta_3$. An angle between the sixteenth surface and the direction along the y-axis may be $\varphi_3$.

$\theta_1$ may be a value of an angle. $\theta_2$ may be a value of an angle. $\theta_3$ may be a value of an angle. $\varphi_1$ may be a value of an angle. $\varphi_2$ may be a value of an angle. $\varphi_3$ may be a value of an angle.

$\theta_1$ may be 30°. $\theta_2$ may be 45°. $\theta_3$ may be 60°. $\varphi_1$ may be 30°. $\varphi_2$ may be 45°. $\varphi_3$ may be 60°.

The surfaces may be arranged as a continuous surface. Each plate may comprise a first flat surface and a second flat surface opposite to the first flat surface of that plate. Each plate may have substantially uniform thickness, i.e. the first and second surfaces of each plate may be substantially parallel to each other. The first flat surfaces of the plates may define a convex surface. The second flat surfaces of the plates may define a concave surface.

In a further aspect, the present invention provides a multi-axis ultrasonic scanner calibration verification tool. The tool comprises: a plurality of mutually oblique plates defining a plurality of mutually oblique planar surfaces, the surfaces being at predefined angles with respect to one another; and a plurality of reference features measurable by a multi-axis ultrasonic scanner. The plates are arranged so as to define a continuous surface. Each plate comprises a first flat surface and a second flat surface opposite to the first flat surface of that plate. Each plate has substantially uniform thickness. The first flat surfaces of the plates define a convex surface. The second flat surfaces of the plates define a concave surface.

In a further aspect, the present invention provides a calibration verification tool for use with a multi-axis ultrasonic scanner, the tool comprising a plurality of mutually oblique planar surfaces, the surfaces being at predefined angles with respect to one another.

In a further aspect, the present invention provides a multi-axis ultrasonic scanner calibration verification tool comprising a plurality of mutually oblique planar surfaces, the surfaces being at predefined angles with respect to one another.

Preferably, the tool comprises at least five mutually oblique surfaces. More preferably, the tool comprises at least ten mutually oblique surfaces. More preferably, the tool comprises at least fifteen (for example, sixteen) mutually oblique surfaces.

An angle between a first surface of the plurality of surfaces and a direction along an x-axis of a Cartesian coordinate system may be 0°. An angle between the first surface and a direction along a y-axis of the Cartesian coordinate system may be 0°. An angle between a second surface of the plurality of surfaces and the direction along the x-axis may be $\theta_1$. An angle between the second surface and the direction along the y-axis may be 0°. An angle between a third surface of the plurality of surfaces and the direction along the x-axis may be $\theta_2$. An angle between the third surface and the direction along the y-axis may be 0°. An angle between a fourth surface of the plurality of surfaces and the direction along the x-axis may be $\theta_3$. An angle between the fourth surface and the direction along the y-axis may be 0°. An angle between a fifth surface of the plurality of surfaces and the direction along the x-axis may be 0°. An angle between the fifth surface and the direction along the y-axis may be $\varphi_1$. An angle between a sixth surface of the plurality of surfaces and the direction along the x-axis may be 0°. An angle between the sixth surface and the direction along the y-axis may be $\varphi_2$. An angle between a seventh surface of the plurality of surfaces and the direction along the x-axis may be 0°. An angle between the seventh surface and the direction along the y-axis may be $\varphi_3$. An angle between a eighth surface of the plurality of surfaces and the direction along the x-axis may be $\theta_1$. An angle between the eighth surface and the direction along the y-axis may be $\varphi_1$. An angle between a ninth surface of the plurality of surfaces and the direction along the x-axis may be $\theta_2$. An angle between the ninth surface and the direction along the y-axis may be $\varphi_1$. An angle between a tenth surface of the plurality of surfaces and the direction along the x-axis may be $\theta_3$. An angle between the tenth surface and the direction along the y-axis may be $\varphi_1$. An angle between a eleventh surface of the plurality of surfaces and the direction along the x-axis may be $\theta_1$. An angle between the eleventh surface and the direction along the y-axis may be $\varphi_2$. An angle between a twelfth surface of the plurality of surfaces and the direction along the x-axis may be $\theta_2$. An angle between the twelfth surface and the direction along the y-axis may be $\varphi_2$. An angle between a thirteenth surface of the plurality of surfaces and the direction along the x-axis may be $\theta_3$. An angle between the thirteenth surface and the direction along the y-axis may be $\varphi_2$. An angle between a fourteenth surface of the plurality of surfaces and the direction along the x-axis may be $\theta_1$. An angle between the fourteenth surface and the direction along the y-axis may be $\varphi_3$. An angle between a fifteenth surface of the plurality of surfaces and the direction along the x-axis may be $\theta_2$. An angle between the fifteenth surface and the direction along the y-axis may be $\varphi_3$. An angle between a sixteenth surface of the plurality of surfaces and the direction along the x-axis may be $\theta_3$. An angle between the sixteenth surface and the direction along the y-axis may be $\varphi_3$.

$\theta_1$ may be a value of an angle. $\theta_2$ may be a value of an angle. $\theta_3$ may be a value of an angle. $\varphi_1$ may be a value of an angle. $\varphi_2$ may be a value of an angle. $\varphi_3$ may be a value of an angle.

$\theta_1$ may be 30°. $\theta_2$ may be 45°. $\theta_3$ may be 60°. $\varphi_1$ may be 30°. $\varphi_2$ may be 45°. $\varphi_3$ may be 60°.

The surfaces may be arranged as a continuous surface.

Each surface may be provided by a respective flat plate. Each plate may comprise a first flat surface and a second flat surface opposite to the first flat surface of that plate. For each plate, the first and second surfaces of that plate may be substantially parallel.

The first flat surfaces of the plates may define a convex surface. The second flat surfaces of the plates may define a concave surface.

The tool may further comprise at least three reference features that are detectable by a multi-axis ultrasonic scanner.

In a further aspect, the present invention provides a method of assessing a calibration of apparatus, the method comprising: providing a calibration verification tool, the tool comprising a plurality of mutually oblique planar surfaces, the surfaces being at predefined angles with respect to one another; measuring, using the apparatus, a physical property of each surface; for each surface, using the measured physical property of that surface, determining an orientation within a reference frame of at least part of the apparatus when the physical property of that surface was measured; and, using the determined orientations, verifying whether or not the apparatus is calibrated such that one or more predetermined criteria are satisfied.

The apparatus may be a multi-axis ultrasonic scanner. The physical property may be a reflected ultrasonic response.

Measuring a physical property of each surface may comprises: providing a digital model of the tool; and, using the digital model, controlling the apparatus to measure the physical property of each surface.

The step of, for each surface, using the measured physical property of that surface, determining an orientation within a reference frame of at least part of the apparatus when the physical property of that surface was measured may comprise, for each surface: comparing the measured physical property of that surface to a predetermined expected measurement value; and, using the comparison, determining the orientation within the reference frame of the at least part of the apparatus when the physical property of that surface was measured.

DETAILED DESCRIPTION

It will be appreciated that relative terms such as horizontal and vertical, upper and lower, and so on are used herein merely for ease of reference to the Figures, and these terms are not limiting as such, and any two differing directions or positions and so on may be implemented rather than truly horizontal and vertical, upper and lower, and so on.

Figure 1:
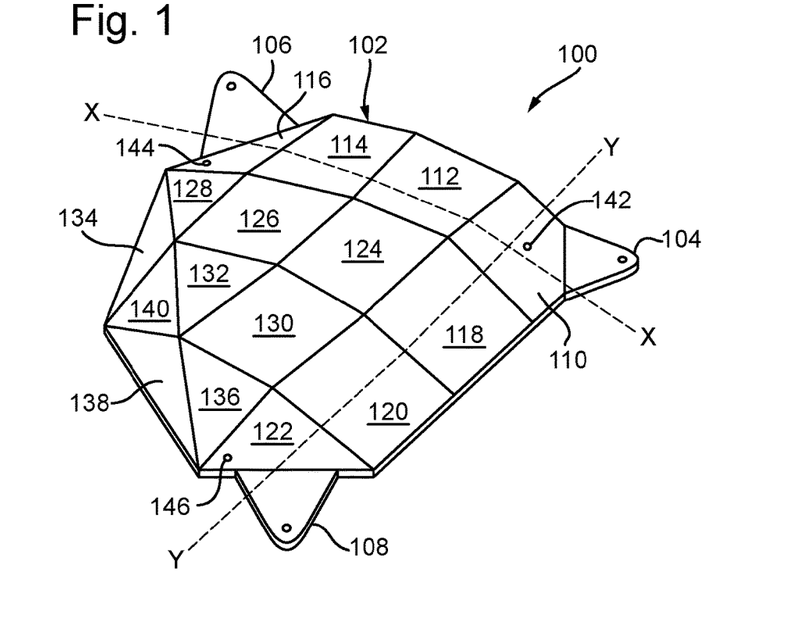
FIG. 1 is a schematic illustration (not to scale) of a perspective view from above of a verification tool.
Figure 2:
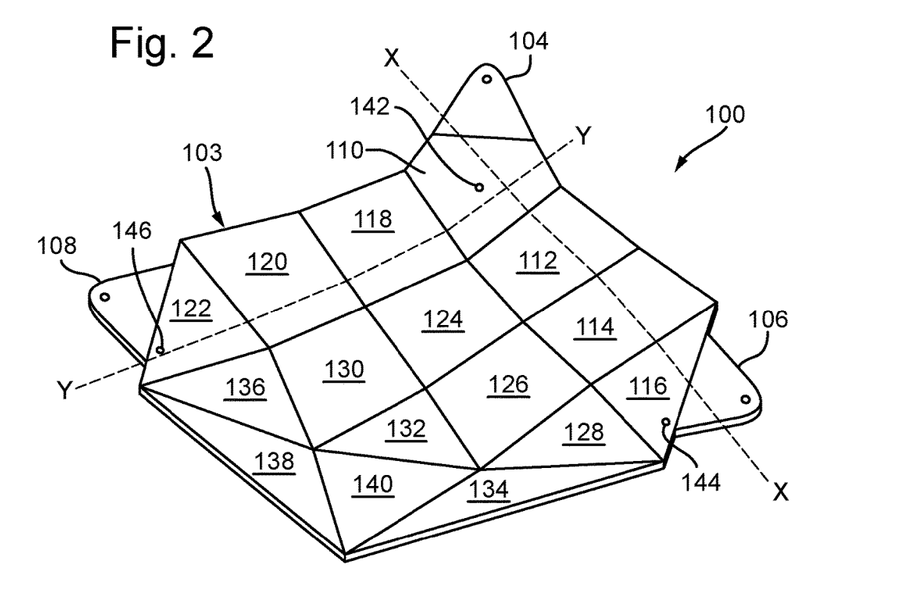
FIG. 2 is a schematic illustration (not to scale) of a perspective view from below of the verification tool.

FIGS. 1 and 2 are schematic illustrations (not to scale) of perspective views of an embodiment of a verification tool 100.

FIG. 1 shows the verification tool 100 as viewed from above such that an upper surface 102 (convex) of the verification tool 100 is visible. FIG. 2 shows the verification tool 100 as viewed from below such that a lower surface 103 (concave) of the verification tool 100 is visible.

As described in more detail later below with reference to FIG. 5, the verification tool 100 is usable for verifying whether or not a multi-axis non-destructive test ultrasonic scanner has been correctly calibrated.

The verification tool 100 comprises a main body portion and three tabs formed about a periphery of the main body portion.

In this embodiment, the verification tool 100 is made of a corrosion resistant metal, for example stainless steel or Titanium. The verification tool 100 is formed as a single piece. For example, the verification tool 100 may be a single forged or cast item, or may be machined from a single item (e.g. using a computer numerical control (CNC) milling machine).

The three tabs, namely the first tab 104, the second tab 106, and the third tab 108 are attached to respective sides of the body portion of the verification tool 100. In this embodiment, the tabs 104-108 are formed such that the lower surfaces of the tabs 104-108 lie in a common plane. Each of the tabs 104-108 comprises a through hole.

In this embodiment, the main body portion of the verification tool 100 is formed of sixteen plates 110-140, namely a first plate 110, a second plate 112, a third plate 114, and so on.

Each of the plates 110-140 is a flat plate such that the upper and lower surfaces of each plate 110-140 are planar and parallel.

In this embodiment, the plates 110-140 form a continuous structure. The upper surface 102 of the structure formed by the plates 110-140 (i.e. the main body of the verification tool 100) is a convex surface. Also, the lower surface 103 of the main body is a concave surface.

In this embodiment, a first side of the main body of the verification tool 100 is formed by the first plate 110, the second plate 112, the third plate 114 and the fourth plate 116.

In this embodiment, a second side of the main body of the verification tool 100 is formed by the first plate 110, the fifth plate 118, the sixth plate 120 and the seventh plate 122.

The first plate 110 is a pentagonal plate having five edges. A first edge of the first plate 110 is connected to a first edge of the second plate 112 such that the connected first and second plates 110, 112 are contiguous. A second edge of the first plate 110 is connected to a first edge of the fifth plate 118 such that the connected first and fifth plates 110, 118 are contiguous. In this embodiment, the first and second edges of the first plate 110 are orthogonal such that the second and fifth plates 112, 118 extend from the first plate orthogonally to one another. A third edge of the first plate 110 defines part of an edge of the verification tool 100 along the second side of the verification tool 100. A fourth edge of the first plate 110 is located opposite to the first and second edges of the first plate. The first tab 104 is connected to the main body of the verification tool along the fourth edge of the first plate 110. A fifth edge of the first plate 110 defines part of an edge of the verification tool 100 along the first side of the verification tool 100.

In this embodiment, the first plate 110 includes a through-hole, hereinafter referred to as a "first reference hole" 142.

The second plate 112 is a quadrilateral plate. The first edge of the second plate 112 is connected to the first edge of the first plate 110 such that the connected first and second plates 110, 112 are contiguous. A second edge of the second plate 112 defines part of the edge of the verification tool 100 along the first side of the verification tool 100. A third edge of the second plate 112 is connected to a first edge of the third plate 114 such that the connected second and third plates 112, 114 are contiguous. A fourth edge of the second plate 112 is connected to a first edge of the eighth plate 124 such that the connected second and eighth plates 112, 124 are contiguous.

The third plate 114 is a quadrilateral plate. The first edge of the third plate 114 is connected to the third edge of the second plate 112 such that the connected second and third plates 112, 114 are contiguous. A second edge of the third plate 114 defines part of the edge of the verification tool 100 along the first side of the verification tool 100. A third edge of the third plate 114 is connected to a first edge of the fourth plate 116 such that the connected third and fourth plates 114, 116 are contiguous. A fourth edge of the third plate 114 is connected to a first edge of the ninth plate 126 such that the connected third and ninth plates 114, 126 are contiguous.

The fourth plate 116 is a triangular plate. The first edge of the fourth plate 116 is connected to the third edge of the third plate 114 such that the connected third and fourth plates 114, 116 are contiguous. A second edge of the fourth plate 116 defines part of the edge of the verification tool 100 along the first side of the verification tool 100. The second tab 106 is connected to the main body of the verification tool 100 along the second edge of the fourth plate 116. A third edge of the fourth plate 116 is connected to a first edge of the tenth plate 128 such that the connected fourth and tenth plates 116, 128 are contiguous.

In this embodiment, the fourth plate 116 includes a through-hole, hereinafter referred to as a "second reference hole" 144.

The fifth plate 118 is a quadrilateral plate. The first edge of the fifth plate 118 is connected to the second edge of the first plate 110 such that the connected first and fifth plates 110, 118 are contiguous. A second edge of the fifth plate 118 defines part of the edge of the verification tool 100 along the second side of the verification tool 100. A third edge of the fifth plate 118 is connected to a first edge of the sixth plate 120 such that the connected fifth and sixth plates 118, 120 are contiguous. A fourth edge of the fifth plate 118 is connected to a second edge of the eighth plate 124 such that the connected fifth and eighth plates 118, 124 are contiguous.

The sixth plate 120 is a quadrilateral plate. The first edge of the sixth plate 120 is connected to the third edge of the fifth plate 118 such that the connected fifth and sixth plates 118, 120 are contiguous. A second edge of the sixth plate 120 defines part of the edge of the verification tool 100 along the second side of the verification tool 100. A third edge of the sixth plate 120 is connected to a first edge of the seventh plate 122 such that the connected sixth and seventh plates 120, 122 are contiguous. A fourth edge of the sixth plate 120 is connected to a first edge of the eleventh plate 130 such that the connected sixth and eleventh plates 120, 130 are contiguous.

The seventh plate 122 is a triangular plate. The first edge of the seventh plate 122 is connected to the third edge of the sixth plate 120 such that the connected sixth and seventh plates 120, 122 are contiguous. A second edge of the seventh plate 122 defines part of the edge of the verification tool 100 along the second side of the verification tool 100. The third tab 108 is connected to the main body of the verification tool 100 along the second edge of the seventh plate 122. A third edge of the seventh plate 122 is connected to a first edge of the fourteenth plate 136 such that the connected seventh and fourteenth plates 122, 136 are contiguous.

In this embodiment, the seventh plate 122 includes a through-hole, hereinafter referred to as a "third reference hole" 146.

The eighth plate 124 is a quadrilateral plate. The first edge of the eighth plate 124 is connected to the fourth edge of the second plate 112 such that the connected second and eighth plates 112, 124 are contiguous. The second edge of the eighth plate 124 is connected to the fourth edge of the fifth plate 118 such that the connected fifth and eighth plates 118, 124 are contiguous. A third edge of the eighth plate 124 is connected to a second edge of the eleventh plate 130 such that the connected eighth and eleventh plates 124, 130 are contiguous. A fourth edge of the eighth plate 124 is connected to the second edge of the ninth plate 126 such that the connected eighth and ninth plates 124, 126 are contiguous.

The ninth plate 126 is a quadrilateral plate. The first edge of the ninth plate 126 is connected to the fourth edge of the third plate 114 such that the connected third and ninth plates 114, 126 are contiguous. The second edge of the ninth plate 126 is connected to the fourth edge of the eighth plate 124 such that the connected eighth and ninth plates 124, 126 are contiguous. A third edge of the ninth plate 126 is connected to a first edge of the twelfth plate 132 such that the connected ninth and twelfth plates 126, 132 are contiguous. A fourth edge of the ninth plate 126 is connected to a second edge of the tenth plate 128 such that the connected ninth and tenth plates 126, 128 are contiguous.

The tenth plate 128 is a triangular plate. The first edge of the tenth plate 128 is connected to the third edge of the fourth plate 116 such that the connected fourth and tenth plates 116, 128 are contiguous. The second edge of the tenth plate 128 is connected to the fourth edge of the ninth plate 126 such that the connected ninth and tenth plates 126, 128 are contiguous. A third edge of the tenth plate 128 is connected to a first edge of the thirteenth plate 134 such that the connected tenth and thirteenth plates 128, 134 are contiguous.

The eleventh plate 130 is a quadrilateral plate. The first edge of the eleventh plate 130 is connected to the fourth edge of the sixth plate 120 such that the connected sixth and eleventh plates 120, 130 are contiguous. The second edge of the eleventh plate 130 is connected to the third edge of the eighth plate 124 such that the connected eighth and eleventh plates 124, 130 are contiguous. A third edge of the eleventh plate 130 is connected to a second edge of the twelfth plate 132 such that the connected eleventh and twelfth plates 130, 132 are contiguous. A fourth edge of the eleventh plate 130 is connected to a second edge of the fourteenth plate 136 such that the connected eleventh and fourteenth plates 130, 136 are contiguous.

The twelfth plate 132 is a triangular plate. The first edge of the twelfth plate 132 is connected to the third edge of the ninth plate 126 such that the connected ninth and twelfth plates 126, 132 are contiguous. The second edge of the twelfth plate 132 is connected to the third edge of the eleventh plate 130 such that the connected eleventh and twelfth plates 130, 132 are contiguous. A third edge of the twelfth plate 132 is connected to a first edge of the sixteenth plate 140 such that the connected twelfth and sixteenth plates 132, 140 are contiguous.

The thirteenth plate 134 is a triangular plate. The first edge of the thirteenth plate 134 is connected to the third edge of the tenth plate 128 such that the connected tenth and thirteenth plates 128, 134 are contiguous. A second edge of the thirteenth plate 134 is connected to a second edge of the sixteenth plate 140 such that the connected thirteenth and sixteenth plates 134, 140 are contiguous. A third edge of the thirteenth plate 134 defines part of an edge of the verification tool 100.

The fourteenth plate 136 is a triangular plate. The first edge of the fourteenth plate 136 is connected to the third edge of the seventh plate 122 such that the connected seventh and fourteenth plates 122, 136 are contiguous. The second edge of the fourteenth plate 136 is connected to the fourth edge of the eleventh plate 130 such that the connected eleventh and fourteenth plates 130, 136 are contiguous. A third edge of the fourteenth plate 136 is connected to a first edge of the fifteenth plate 138 such that the connected fourteenth and fifteenth plates 136, 138 are contiguous.

The fifteenth plate 138 is a triangular plate. The first edge of the fifteenth plate 138 is connected to the third edge of the fourteenth plate 136 such that the connected fourteenth and fifteenth plates 136, 138 are contiguous. A second edge of the fifteenth plate 138 is connected to a third edge of the sixteenth plate 140 such that the connected fifteenth and sixteenth plates 138, 140 are contiguous. A third edge of the fifteenth plate 138 defines part of an edge of the verification tool 100.

The sixteenth plate 140 is a triangular plate. The first edge of the sixteenth plate 140 is connected to the third edge of the twelfth plate 132 such that the connected twelfth and sixteenth plates 132, 140 are contiguous. The second edge of the sixteenth plate 140 is connected to the second edge of the thirteenth plate 134 such that the connected thirteenth and sixteenth plates 134, 140 are contiguous. The third edge of the sixteenth plate 140 is connected to the second edge of the fifteenth plate 138 such that the connected fifteenth and sixteenth plates 138, 140 are contiguous.

In this embodiment, the plates 110-140 are of uniform thickness such that, for each of the plates 110-140, the upper and lower surfaces of that plate are parallel to each other.

In this embodiment the plates 110-140 are mutually oblique.

Figure 3:
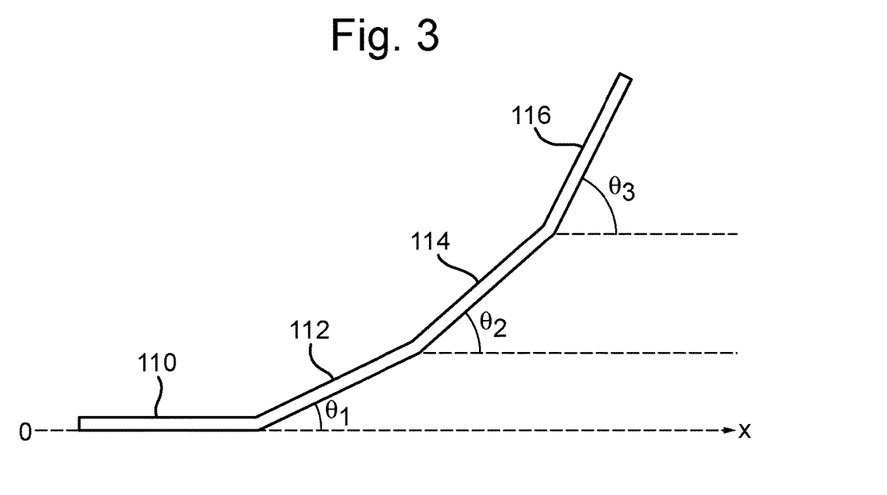
FIG. 3 is a schematic illustration (not to scale) of a cross-section of the verification tool.

FIG. 3 is a schematic illustration (not to scale) showing a cross section through the line X-X shown in FIGS. 1 and 2. Thus, FIG. 3 shows a cross section along the first side of the verification tool 100, i.e. through the first plate 110, the second plate 112, the third plate 114, and the fourth plate 116.

Figure 4:
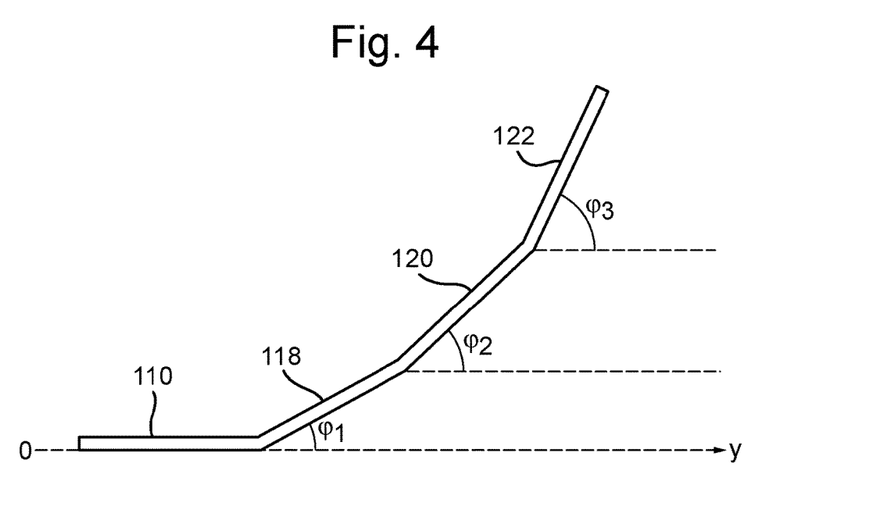
FIG. 4 is a schematic illustration (not to scale) of a further cross-section of the verification tool.

FIG. 4 is a schematic illustration (not to scale) showing a cross section through the line Y-Y shown in FIGS. 1 and 2. Thus, FIG. 4 shows a cross section along the second side of the verification tool 100, i.e. through the first plate 110, the fifth plate 118, the sixth plate 120, and the seventh plate 122.

In this embodiment, the line X-X lies in the plane y=0 of a Cartesian coordinate system. In some embodiments, the line X-X may define an x-axis of the Cartesian coordinate system.

In this embodiment, the line Y-Y lies in the plane x=0 of the Cartesian coordinate system. In some embodiments, the line Y-Y may define a y-axis of the Cartesian coordinate system. The line X-X is orthogonal to the line Y-Y.

The upper surface of the first plate 110 lies in the x-y plane (i.e. z=0) of the Cartesian coordinate system. In other words, an angle between the first plate 110 and a direction along the x-axis is 0°. Also, an angle between the first plate 110 and a direction along the y-axis is 0°.

As shown in FIG. 3, an angle between the upper surface of the second plate 112 and a direction along the x-axis is $\theta_1$. Also, an angle between the upper surface of the second plate 112 and a direction along the y-axis is 0°.

As shown in FIG. 3, an angle between the upper surface of the third plate 114 and a direction along the x-axis is $\theta_2$. Also, an angle between the upper surface of the third plate 114 and a direction along the y-axis is 0°.

As shown in FIG. 3, an angle between the upper surface of the fourth plate 116 and a direction along the x-axis is $\theta_3$. Also, an angle between the upper surface of the fourth plate 116 and a direction along the y-axis is 0°.

As shown in FIG. 4, an angle between the upper surface of the fifth plate 118 and a direction along the y-axis is $\varphi_1$. Also, an angle between the upper surface of the fifth plate 118 and a direction along the x-axis is 0°.

As shown in FIG. 4, an angle between the upper surface of the sixth plate 120 and a direction along the y-axis is $\varphi_2$. Also, an angle between the upper surface of the sixth plate 120 and a direction along the x-axis is 0°.

As shown in FIG. 4, an angle between the upper surface of the seventh plate 122 and a direction along the y-axis is $\varphi_3$. Also, an angle between the upper surface of the seventh plate 122 and a direction along the x-axis is 0°.

In this embodiment, an angle between the upper surface of the eighth plate 124 and a direction along the x-axis is $\theta_1$. Also, an angle between the upper surface of the eighth plate 124 and a direction along the y-axis is $\varphi_1$.

In this embodiment, an angle between the upper surface of the ninth plate 126 and a direction along the x-axis is $\theta_2$. Also, an angle between the upper surface of the ninth plate 126 and a direction along the y-axis is $\varphi_1$.

In this embodiment, an angle between the upper surface of the tenth plate 128 and a direction along the x-axis is $\theta_3$. Also, an angle between the upper surface of the tenth plate 128 and a direction along the y-axis is $\varphi_1$.

In this embodiment, an angle between the upper surface of the eleventh plate 130 and a direction along the x-axis is $\theta_1$. Also, an angle between the upper surface of the eleventh plate 130 and a direction along the y-axis is $\varphi_2$.

In this embodiment, an angle between the upper surface of the twelfth plate 132 and a direction along the x-axis is $\theta_2$. Also, an angle between the upper surface of the twelfth plate 132 and a direction along the y-axis is $\varphi_2$.

In this embodiment, an angle between the upper surface of the thirteenth plate 134 and a direction along the x-axis is $\theta_3$. Also, an angle between the upper surface of the thirteenth plate 134 and a direction along the y-axis is $\varphi_2$.

In this embodiment, an angle between the upper surface of the fourteenth plate 136 and a direction along the x-axis is $\theta_1$. Also, an angle between the upper surface of the fourteenth plate 136 and a direction along the y-axis is $\varphi_3$.

In this embodiment, an angle between the upper surface of the fifteenth plate 138 and a direction along the x-axis is $\theta_2$. Also, an angle between the upper surface of the fifteenth plate 138 and a direction along the y-axis is $\varphi_3$.

In this embodiment, an angle between the upper surface of the sixteenth plate 140 and a direction along the x-axis is $\theta_3$. Also, an angle between the upper surface of the sixteenth plate 140 and a direction along the y-axis is $\varphi_3$.

In this embodiment, $\theta_1$ is 30°. Also, $\theta_2$ is 45°. Also, $\theta_3$ is 60°. However, in other embodiments, one or more of the angles $\theta_1$, $\theta_2$, or $\theta_3$ may be a different appropriate angle.

In this embodiment, $\varphi_1$ is 30°. Also, $\varphi_2$ is 45°. Also, $\varphi_3$ is 60°. However, in other embodiments, one or more of the angles $\varphi_1$, $\varphi_2$, or $\varphi_3$ may be a different appropriate angle.

An example method of using the above described verification tool 100 to verify whether or not a multi-axis ultrasonic scanner is correctly calibrated will now be described.

Figure 5:
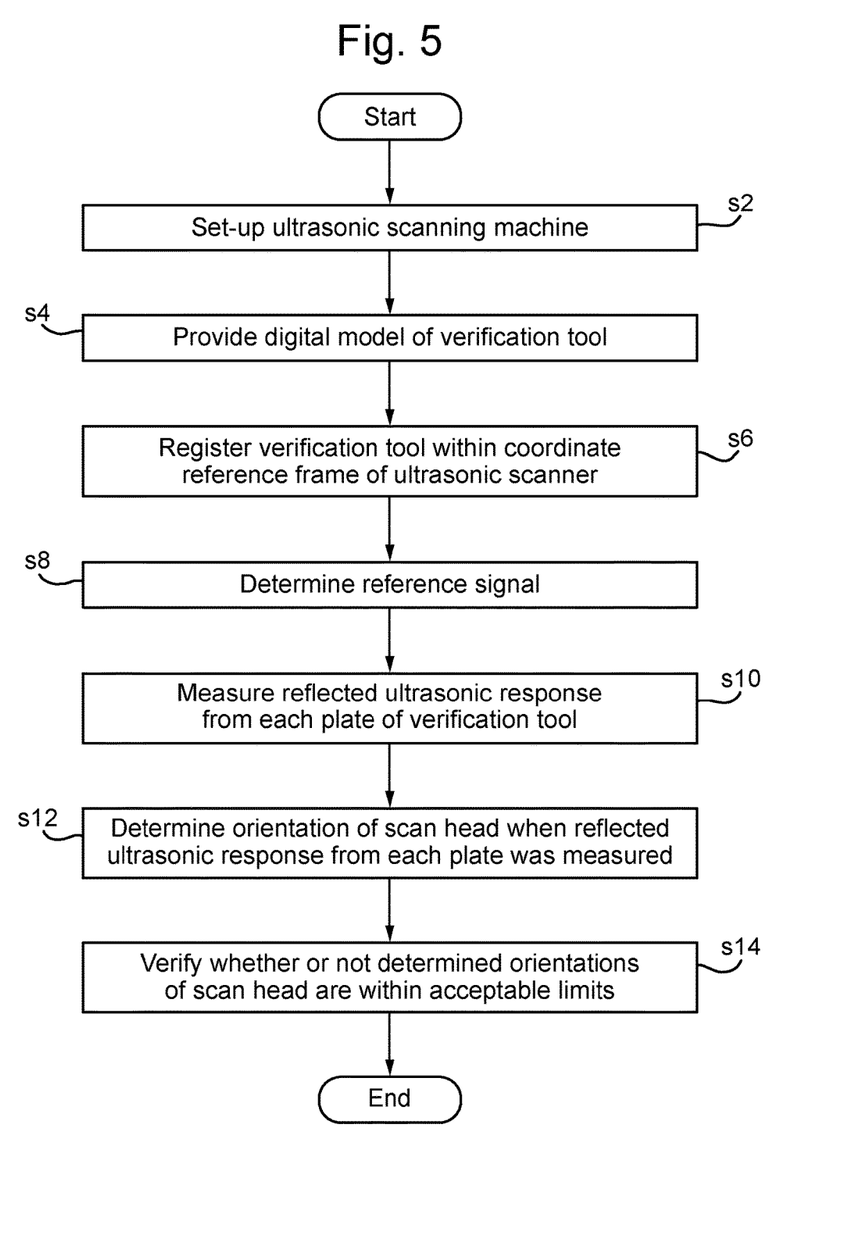
FIG. 5 is a process flow chart showing certain steps of a process of using the verification tool to verifying whether or not a multi-axis ultrasonic scanner is correctly calibrated.

FIG. 5 is a process flow chart showing certain steps of a process of verifying whether or not a multi-axis ultrasonic scanner is correctly calibrated.

At s2, the ultrasonic scanning machine is set-up in terms of approximated kinematic models and reference angles with respect to the orthogonal scanning planes to the linear x-, y-, and z-axes.

At step s4, a digital model of the verification tool 100 is defined.

The digital model of the verification tool 100 is stored by the ultrasonic scanner. The digital model is defined with respect to a coordinate reference frame of the ultrasonic scanner. In this embodiment, the digital model is a CATIA generated profile for the verification tool 100.

At step s6, the ultrasonic device registers the verification tool 100 within its coordinate reference frame.

In this embodiment, registration of the verification tool is performed as follows. Firstly, the verification tool 100 is fixedly secured relative to the ultrasonic scanner by positioning respective locator pins through the through holes of the tabs 104, 106, 108. The ultrasonic scanner then measures the relative positions of the first, second, and third reference holes 142, 144, 146 of the verification tool 100. The ultrasonic scanner then registers the measured reference holes 142 144, 146 with corresponding respective digital reference holes defined in the digital model of the verification tool 100. Thus, the position of the verification tool 100 within the coordinate reference frame of the ultrasonic scanner is determined. In this embodiment, the position of the verification tool 100 within the coordinate reference frame is a CATIA derived set of coordinates.

At s8, the scan head of the ultrasonic scanner is driven to any of the plates 110-140 of the verification tool 100 (e.g. that which exhibits an angle of presentation nearest to 0×0 degrees with respect to the major scanning plane of the ultrasonic scanner), and a reference signal is established by optimising the response from that plate 110-140 (for example, the direct reflected ultrasonic response from that plate 110-140). This measured reference signal may be used as a baseline measurement against which further measurements taken at step s10 below may be compared.

Control of the multi-axis ultrasonic scanner may be performed using the digital model of the verification tool 100. In some embodiments, registration of the verification tool 100 results both the digital model of the tool 100 and the tool 100 having known locations with respect to coordinate reference frame of the ultrasonic scanner. For example, the tool 100 and the digital model may be collocated in the coordinate reference frame. Thus, by moving the multi-axis ultrasonic scanner with respect to the digital model, the ultrasonic scanner is moved correspondingly with respect to the tool 100.

At step s10, for each plate 110-140 of the verification tool 100 in turn, a controller of the ultrasonic scanner uses the CATIA derived set of coordinates of the verification tool 100 to drive the scan head of the ultrasonic scanner on to the upper (and/or lower) surface of that plate 110-140 and measure a direct reflected ultrasonic response from that plate 110-140 and/or measure the transmitted ultrasonic signal from one side of the scanner, through the verification tool 100 to the other side of the scanner.

The measurement of the ultrasonic responses from the upper and lower surfaces of a plate, and the measurement of a transmitted ultrasonic signal through that plate, are effectively measurements of physical properties of that plate. Measurements of these physical properties advantageously tends to provide for improved calibration of the ultrasonic scanner. Also, use of more than one or these different measurements (e.g. measurement of the ultrasonic responses from a surface of a plate and the measurement of the transmitted ultrasonic signal through that plate) advantageously tends to provide for improved calibration of the ultrasonic scanner.

The measured responses may be compared to the baseline measurement taken at step s8 above.

At step s12, for each plate 110-140 of the verification tool 100, a processor (which is operatively connected to the ultrasonic scanner) uses the measured reflected ultrasonic response from that plate 110-140 to determine the orientation of the scan head of the ultrasonic scanner, relative to the reference frame, when the scan head measured the reflected ultrasonic response from that plate 110-140. In this embodiment, the rotational movement of the scan head when it measured the reflected ultrasonic response from a plate 110-140 is determined by comparing the measured reflected ultrasonic response from that plate 110-140 to a predetermined optimum response (e.g. the baseline measurement taken at step s8 above).

At step s14, for each plate 110-140 of the verification tool 100, the processor determines whether or not the orientation of the scan head of the ultrasonic scanner when that plate 110-140 was measured is within pre-determined limits.

If, for each plate 110-140, the determined orientation for the scan head is within an acceptable range, the processor determines that the ultrasonic scanner is correctly calibrated.

However, if, for one or more of the plates 110-140, the determined orientation for the scan head is not within the acceptable range, the processor determines that the ultrasonic scanner is not correctly calibrated. If the ultrasonic scanner is determined to be incorrectly calibrated, a re-calibration process may be performed, and the verification process may be repeated.

Thus, a process of verifying whether or not a multi-axis ultrasonic scanner is correctly calibrated is provided.

Advantageously, the above described verification tool tends to be useable to provide practical evidence for verification of calibration and control of rotational axes for an automated ultrasonic scanning machine.

The above described verification tool tends to be relatively simple to use, and produces easily comprehensible results, for example, compared to using mathematical design, parameters of gearing ratios and/or kinematic models of an ultrasonic scanning machine.

The above described verification tool has parallel upper and lower surfaces. Thus, advantageously, the verification tool may be used in either a single-sided mode or a double-sided mode. In the single-sided mode, the scan head of the multi-axis ultrasonic scanner may be driven against one surface (upper or lower) of the verification tool. In the double-sided mode, scan heads may simultaneously be driven against corresponding points on both surfaces (i.e. upper and lower) of the verification tool. Such double-sided use of the verification tool may be used to assess the 'through transmission' alignment of the ultrasonic scanner.

The above described verification tool may define a quarter of a hemisphere. Thus, in some verification processes, the verification tool may be rotated three times to represent each quadrant of the hemisphere, and provide full hemispherical testing. In other embodiments, the verification tool is not rotated, or rotated a different number of times, e.g. twice.

The above described verification tool tends to be particularly useful in the assessment of new equipment, such as new ultrasonic scanners. The verification tool is relatively portable, robust, stable and practical to use in a factory environment and for transportation between factories.

Apparatus, including the above mentioned processor and or controller, for performing a method step described above may be provided by configuring or adapting any suitable apparatus, for example one or more computers or other processing apparatus or processors, and/or providing additional modules. The apparatus may comprise a computer, a network of computers, or one or more processors, for implementing instructions and using data, including instructions and data in the form of a computer program or plurality of computer programs stored in or on a machine readable storage medium such as computer memory, a computer disk, ROM, PROM etc., or any combination of these or other storage media.

It should be noted that certain of the process steps depicted in the flowchart of FIG. 5 and described above may be omitted or such process steps may be performed in differing order to that presented above and shown in FIG. 5. Furthermore, although all the process steps have, for convenience and ease of understanding, been depicted as discrete temporally-sequential steps, nevertheless some of the process steps may in fact be performed simultaneously or at least overlapping to some extent temporally.

In the above embodiments, the verification tool is used to verify whether or not a multi-axis ultrasonic scanner is correctly calibrated. The verification tool is used to verify rotary axes movement of the ultrasonic scanner. However, in other embodiments, the verification tool is used for a different purpose.

As an example, the verification tool may be used to verify a kinematic model (i.e. a mathematical description of the physical parameters and set-up of a combined rotational manipulation system). The verification tool may be used to set absolute angles of the kinematic model in terms of the relevant reference planes defined by the linear orthogonal axis system.

As a further example, the verification tool may be used to verify whether or not a different type of apparatus, i.e. other than a multi-axis ultrasonic scanner, is correctly calibrated. For example, in some embodiments, the verification tool is used to verify whether or not a multi-axis coordinate measuring machine (CMM) is correctly calibrated. In such embodiment, the machine under test may measure a different physical property of each of the plates of the verification tool instead of or in addition to reflected ultrasonic response. In some embodiments, a physical property of the lower surface of one or more of the plates is measured instead of or in addition to a physical property of the upper surface of that plate.

A physical property may be any property that is measurable and whose value describes a physical system's state. Physical properties of an object may include, but are not limited to: absorption, area, capacitance, colour, electric field, intensity, irradiance, location, luminance, magnetic field, opacity, reflectivity, and refractive index.

In the above embodiments, the verification tool comprises sixteen mutually oblique plates. However, in other embodiments, the verification tool comprises a different number of mutually oblique plates. Preferably, the verification tool comprises greater than five mutually oblique plates. More preferably, the verification tool comprises greater than ten mutually oblique plates. More preferably, the verification tool comprises greater than fifteen mutually oblique plates.

The above described verification tool may have any appropriate dimensions which may depend on the objective of the particular verification tool with respect to the type of the machine undergoing verification.

What is claimed is:

1. A method of assessing a calibration of a multi-axis ultrasonic scanner, the method comprising:
providing a calibration verification tool, the tool comprising at least three mutually oblique plates defining a plurality of mutually oblique planar surfaces, the surfaces being at predefined angles with respect to one another;
providing a digital model of the tool defined in a coordinate reference frame of the multi-axis ultrasonic scanner;
registering, by the multi-axis ultrasonic scanner, the tool within the coordinate reference frame of the multi-axis ultrasonic scanner;
using the digital model, controlling the multi-axis ultrasonic scanner to measure a physical property of one of the plates of the tool, thereby determining a reference signal;
for each plate in the plurality of mutually oblique plates, using the digital model, controlling the multi-axis ultrasonic scanner to measure the physical property of that plate;
for each plate in the plurality of mutually oblique plates, using the reference signal and the measured physical property of that plate, determining an orientation within the coordinate reference frame of at least part of the multi-axis ultrasonic scanner when the physical property of that plate was measured; and
using the determined orientations, verifying whether or not the multi-axis ultrasonic scanner is calibrated according to whether or not one or more predetermined criteria are satisfied.

2. The method according to claim 1, wherein measuring the physical property of the plate to determine the reference signal includes optimising a received response from that plate.

3. The method according to claim 1, wherein the physical property is a direct reflected ultrasonic response.

4. The method according to claim 1, wherein:
each of the plates comprises opposing upper and lower surfaces; and
measuring the physical property of the plate includes measuring the physical property from both the upper and lower surfaces of that plate.

5. The method according to claim 1, wherein measuring the physical property of the plate includes measuring an ultrasonic signal transmitted through that plate.

6. The method according to claim 1, wherein determining the orientations comprises, for each of the plates in the plurality of mutually oblique plates:
comparing the measured physical property of that plate to the reference signal; and based on the comparison, determining the orientation within the reference frame of the at least part of the multi-axis ultrasonic scanner when the physical property of that plate was measured.

7. The method according to claim 1, wherein:
the calibration verification tool further comprises a plurality of reference features;
the digital model comprises a plurality of digital reference features, the digital reference features having positions on the digital model that are equivalent to positions of the corresponding reference features on the tool; and
the step of registering comprises:
measuring, by the multi-axis ultrasonic scanner, the positions of the reference features; and
registering the measured reference features with the digital reference features, thereby determining a position of the tool in the coordinate reference frame of the multi-axis ultrasonic scanner.

8. A system comprising:
a calibration verification tool, the tool comprising at least three mutually oblique plates defining a plurality of mutually oblique planar surfaces, the surfaces being at predefined angles with respect to one another;
one or more processors configured for implementing instructions and using data stored in or on a machine readable storage medium;
a digital model of the tool defined in a coordinate reference frame of the multi-axis ultrasonic scanner and stored as at least one of instructions and data in or on the machine readable storage medium;
a controller operatively coupled to the one or more processors, the controller configured to:
control the multi-axis ultrasonic scanner to register the tool within the coordinate reference frame of the multi-axis ultrasonic scanner;
using the digital model, control the multi-axis ultrasonic scanner to measure a physical property of one of the plates of the tool, thereby determining a reference signal; and
for each plate in the plurality of mutually oblique plates, using the digital model, control the multi-axis ultrasonic scanner to measure the physical property of that plate;
wherein the one or more processors are configured to:
for each of the plates in the plurality of mutually oblique plates, using the reference signal and the measured physical property of that plate, determine an orientation within the coordinate reference frame of at least part of the multi-axis ultrasonic scanner when the physical property of that plate was measured; and
using the determined orientations, verify whether or not the multi-axis ultrasonic scanner is calibrated according to whether or not one or more predetermined criteria are satisfied.

9. The system according to claim 8, wherein the calibration verification tool comprises at least sixteen mutually oblique plates.

10. The system according to claim 9, wherein:
an angle between a first surface of the plurality of surfaces and a direction along an x-axis of a Cartesian coordinate system is 0°;
an angle between the first surface and a direction along a y-axis of the Cartesian coordinate system is 0°;
an angle between a second surface of the plurality of surfaces and the direction along the x-axis is $\theta_1$;
an angle between the second surface and the direction along the y-axis is 0°;
an angle between a third surface of the plurality of surfaces and the direction along the x-axis is $\theta_2$;
an angle between the third surface and the direction along the y-axis is 0°;
an angle between a fourth surface of the plurality of surfaces and the direction along the x-axis is $\theta_3$;
an angle between the fourth surface and the direction along the y-axis is 0°;
an angle between a fifth surface of the plurality of surfaces and the direction along the x-axis is 0°;
an angle between the fifth surface and the direction along the y-axis is $\varphi_1$;
an angle between a sixth surface of the plurality of surfaces and the direction along the x-axis is 0°;
an angle between the sixth surface and the direction along the y-axis is $\varphi_2$;
an angle between a seventh surface of the plurality of surfaces and the direction along the x-axis is 0°;
an angle between the seventh surface and the direction along the y-axis is $\varphi_3$;
an angle between a eighth surface of the plurality of surfaces and the direction along the x-axis is $\theta_1$;
an angle between the eighth surface and the direction along the y-axis is $\varphi_1$;
an angle between a ninth surface of the plurality of surfaces and the direction along the x-axis is $\theta_2$;
an angle between the ninth surface and the direction along the y-axis is $\varphi_1$;
an angle between a tenth surface of the plurality of surfaces and the direction along the x-axis is $\theta_3$;
an angle between the tenth surface and the direction along the y-axis is $\varphi_1$;
an angle between a eleventh surface of the plurality of surfaces and the direction along the x-axis is $\theta_1$;
an angle between the eleventh surface and the direction along the y-axis is $\varphi_2$;
an angle between a twelfth surface of the plurality of surfaces and the direction along the x-axis is $\theta_2$;
an angle between the twelfth surface and the direction along the y-axis is $\varphi_2$;
an angle between a thirteenth surface of the plurality of surfaces and the direction along the x-axis is $\theta_3$;
an angle between the thirteenth surface and the direction along the y-axis is $\varphi_2$;
an angle between a fourteenth surface of the plurality of surfaces and the direction along the x-axis is $\theta_1$;
an angle between the fourteenth surface and the direction along the y-axis is $\varphi_3$;
an angle between a fifteenth surface of the plurality of surfaces and the direction along the x-axis is $\theta_2$;
an angle between the fifteenth surface and the direction along the y-axis is $\varphi_3$;
an angle between a sixteenth surface of the plurality of surfaces and the direction along the x-axis is $\theta_3$; and
an angle between the sixteenth surface and the direction along the y-axis is $\varphi_3$.

11. The system according to claim 10, wherein:
$\theta_1$ is 30°;
$\theta_2$ is 45°;
$\theta_3$ is 60°;
$\varphi_1$ is 30°;
$\varphi_2$ is 45°; and
$\varphi_3$ is 60°.

12. The system according to claim 8, wherein the surfaces are arranged as a continuous surface.

13. The system according to claim 8, wherein:
each of the plates comprises a first flat surface and a second flat surface opposite to the first flat surface of that plate; and
each of the plates has a substantially uniform thickness.

14. The system according to claim 13, wherein:
the first flat surfaces of the plates define a convex surface; and
the second flat surfaces of the plates define a concave surface.

* * * * *